(12) United States Patent
Jamal

(10) Patent No.: US 11,364,339 B2
(45) Date of Patent: Jun. 21, 2022

(54) INFUSION UNIT

(71) Applicant: Aamir Zain Jamal, Claremont, CA (US)

(72) Inventor: Aamir Zain Jamal, Claremont, CA (US)

( * ) Notice: Subject to any disclaimer, the term of this patent is extended or adjusted under 35 U.S.C. 154(b) by 184 days.

(21) Appl. No.: 16/913,486

(22) Filed: Jun. 26, 2020

(65) Prior Publication Data
US 2021/0008281 A1    Jan. 14, 2021

Related U.S. Application Data

(60) Provisional application No. 62/873,109, filed on Jul. 11, 2019.

(51) Int. Cl.
*A61M 5/168* (2006.01)
*A61M 5/315* (2006.01)
(Continued)

(52) U.S. Cl.
CPC .... *A61M 5/16836* (2013.01); *A61M 5/14244* (2013.01); *A61M 5/162* (2013.01);
(Continued)

(58) Field of Classification Search
CPC ............... A61M 5/14; A61M 5/142; A61M 2205/3331; A61M 2205/33; A61M 5/168; A61M 5/16831; A61M 5/315; A61M 5/31565; A61M 5/36; A61M 2005/14208; A61M 2205/3334; A61M 2205/3584; A61M 2205/505; A61M 2205/8206; A61M 2230/04; A61M 2230/06; A61M 2230/205; A61M 2230/30; A61M 5/14244;
(Continued)

(56) References Cited

U.S. PATENT DOCUMENTS

| 4,345,595 A * | 8/1982 | Whitney ........... A61M 5/14546 604/152 |
| 4,544,369 A | 10/1985 | Skakoon et al. |
| 4,551,136 A * | 11/1985 | Mandl ................ A61M 5/1483 604/141 |
| 4,585,439 A | 4/1986 | Michel |

(Continued)

FOREIGN PATENT DOCUMENTS

| WO | WO1995/000191 | 1/1995 | |
| WO | WO-9500191 A1 * | 1/1995 | ........ A61M 5/14244 |

(Continued)

*Primary Examiner* — Jason E Flick
(74) *Attorney, Agent, or Firm* — Kirk A. Buhler; Buhler & Associates Patenting

(57) ABSTRACT

Improvements in an infusion unit are disclosed. The infusion unit is a portable pump that can be used with patient that have wrist access or decubital PICC/MID-LINES without the risk of line accidently getting pulled. The infusion unit is in the shape of a conveniently shell that has an appearance of an arm cast. There are no hoses that extend beyond the body of the infusion unit and any vein penetration is completely covered under the body of the infusion unit. The secure enclosed unit prevents unauthorized tampering and entry into the unit. The medication dosing can be remotely monitored, fusion resumed, changed by nursing and the patient. The infusion unit has a wireless connection to a network to adjust medication and monitor vital signs, namely heart rate, O2 level and blood pressure that can be monitored and recorded for review.

20 Claims, 9 Drawing Sheets

Figures 1, 2:
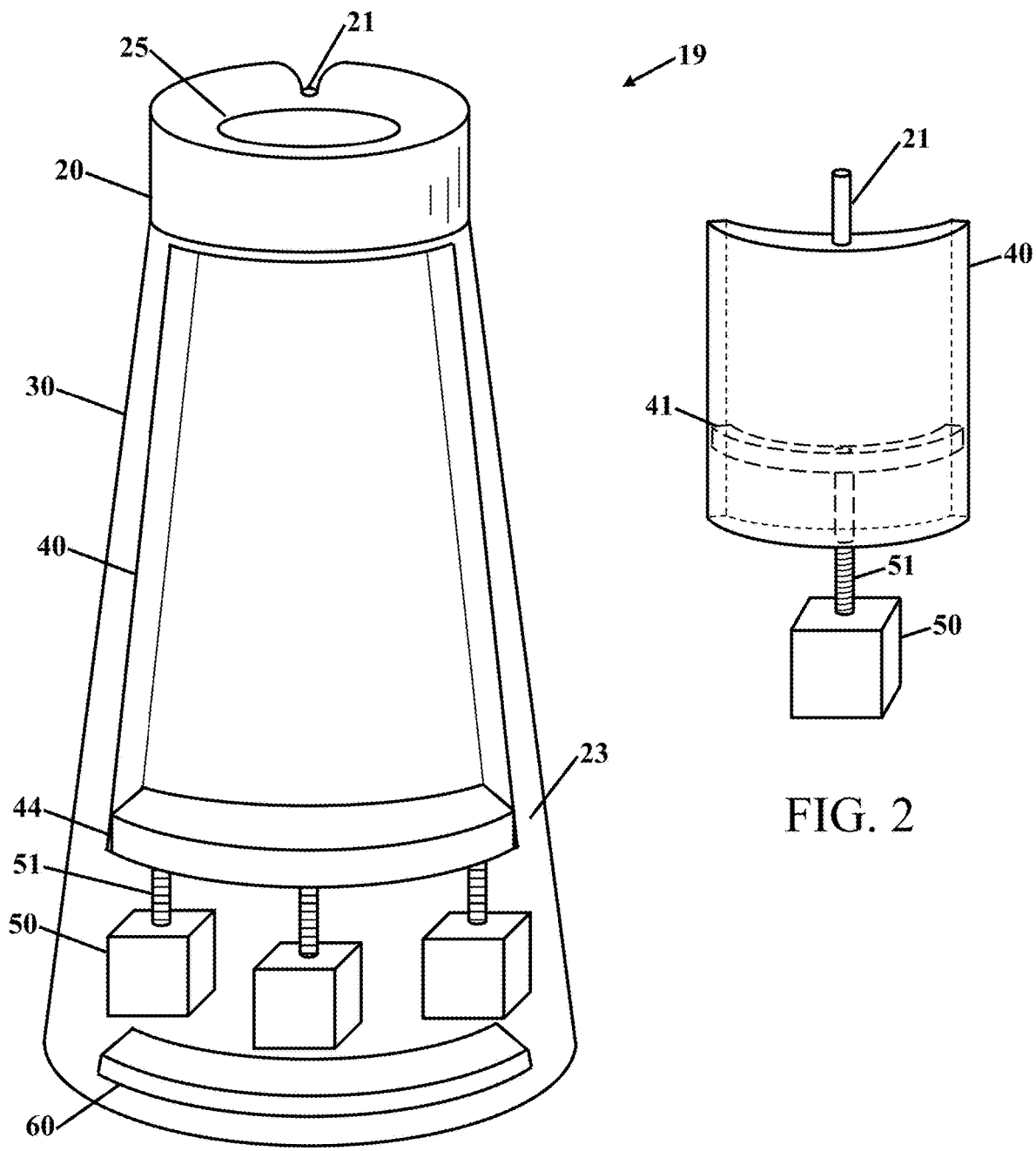

(51) Int. Cl.
*A61M 5/142* (2006.01)
*A61M 5/36* (2006.01)
*A61M 5/162* (2006.01)

(52) U.S. Cl.
CPC ........ *A61M 5/31576* (2013.01); *A61M 5/365* (2013.01); *A61M 2005/14208* (2013.01); *A61M 2205/18* (2013.01); *A61M 2205/3334* (2013.01); *A61M 2205/3584* (2013.01); *A61M 2205/505* (2013.01); *A61M 2205/581* (2013.01); *A61M 2205/583* (2013.01); *A61M 2205/6054* (2013.01); *A61M 2205/6072* (2013.01); *A61M 2205/8206* (2013.01); *A61M 2230/04* (2013.01); *A61M 2230/06* (2013.01); *A61M 2230/205* (2013.01); *A61M 2230/30* (2013.01)

(58) Field of Classification Search
CPC .............. A61M 5/162; A61M 5/16836; A61M 5/31576; A61M 5/365
See application file for complete search history.

(56) References Cited

U.S. PATENT DOCUMENTS

| | | | |
|---|---|---|---|
| 5,221,268 A | 6/1993 | Barton et al. | |
| 5,330,431 A * | 7/1994 | Herskowitz | A61M 5/148 604/153 |
| 5,368,570 A | 11/1994 | Thompson et al. | |
| 6,200,293 B1 | 3/2001 | Kriesel et al. | |
| 6,537,250 B1 | 3/2003 | Kriesel | |
| 8,696,632 B2 | 4/2014 | Gillespie, Jr. et al. | |
| 2008/0167616 A1* | 7/2008 | Veiby | A61M 5/148 604/246 |
| 2009/0203329 A1* | 8/2009 | White | G16H 40/20 604/151 |
| 2014/0228758 A1* | 8/2014 | Chi | A61M 5/152 604/132 |
| 2016/0199576 A1* | 7/2016 | Savage | A61M 5/1415 604/66 |

FOREIGN PATENT DOCUMENTS

| | | | |
|---|---|---|---|
| WO | WO2018096408 | 5/2018 | |
| WO | WO-2018096408 A1 * | 5/2018 | ............ A61M 39/24 |

* cited by examiner

INFUSION UNIT

CROSS REFERENCE TO RELATED APPLICATIONS

This application claims the benefit of Provisional Application Ser. No. 62/873,109 filed Jul. 11, 2019 the entire contents of which is hereby expressly incorporated by reference herein.

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC

Not Applicable

BACKGROUND OF THE INVENTION

Field of the Invention

This invention relates to improvements in infusing drugs into a person. More particularly, the present infusion unit is a self-contained infusion unit having drugs and a power supply that is secured around the arm of a user where a needle is inserted into the vein of a person so the drugs can be infused into the person.

Description of Related Art Including Information Disclosed Under 37 CFR 1.97 and 1.98

At one time or another most people will require medical attention where an intravenous needle is inserted into a vein of a person and drugs, nutrition or medication is slowly infused into the person. All antibiotics and saline and other fluids are given to the patients to directly introduce medications in the blood streams to have more prompt and effective response. Pumps are used in the hospital where nurses will monitor and give medications via pole hanging bags of meds and large pumps to infuse. Sending a patient home need nurses to go to the houses two to three times a day to give meds via IV into the wrist of a patient or through PICC lines. The most common method is to hang a bag containing the medication and infuse the drugs through a long hose. This can cause several problems for mobility of the person and replacing many drugs requires a physician or other medical person to properly and safely make changes. For these reasons, infusion units are mostly used only within a medical facility. Even within a hospital mobility of a person can be a problem when a patient needs to exit a bed to use a bathroom, or walk down a hallway.

A number of patents and or publications have been made to address these issues. Exemplary examples of patents and or publication that try to address this/these problem(s) are identified and discussed below.

U.S. Pat. No. 8,696,632 issued on Apr. 15, 2014 to John Gillespie Jr., and is titled Infusion Pump with Battery Operation Capability. This patent discloses an infusion pump includes a housing; a user interface carried by the housing; a pump actuator positioned by the housing so as to be able to actuate a medical fluid pump member; and wherein the user interface and the pump actuator are powered interchangeably by a rechargeable battery unit configured to power the user interface and the pump actuator at a place for which outside power is unavailable. While this patent is for a portable infusion device the hose runs from the unit to the arm of the person and is subject to pulling and tampering.

U.S. Pat. No. 4,544,369 issued on Oct. 1, 1985 to James G. Skakoon et al., and is titled Battery-Operated Miniature Syringe Infusion Pump. This patent discloses a small, lightweight, battery operated, fixed speed syringe infusion pump is capable of being IV pole mounted. A disposable syringe is secured in a snap-in holder and the syringe plunger is moved by a pusher. The pusher is advanced to the syringe plunger by squeezing a finger tab. This simultaneously decouples the pusher from the internal drive and opens the antisiphon catch to allow quick and easy set-up. This is a pole mounted infusion pump and is transported on a person.

U.S. Pat. No. 4,585,439 issued on Apr. 29, 1986 to Peter Michel and is titled Portable Infusion Unit. This patent discloses a driver sleeve is pivoted in the casing of the unit which is driven by a motor controlled by a control device and supplied by a battery. A threaded rod forming the piston rod of an injection ampule is placed into the driver sleeve in a non-rotary but longitudinally shiftable fashion. A threaded rod is placed into the piston and drives the piston to force fluid out of the injectable ampule. While this patent covers a powered and controlled injection of medication from an ampule it is not battery powered nor configured to be mounted on the arm of a patient.

What is needed is an infusion unit that is secured to an arm of a user where the connection to the vein of the patient is protected and secured. The proposed infusion unit solves this problem with a device that is similar to a cast with an internal power supply, communications system and medication and distribution syringes.

BRIEF SUMMARY OF THE INVENTION

It is an object of the infusion unit to be a portable pump that can be used with patient that have wrist access or decubital PICC/MID-LINES without the risk of line accidently getting pulled. The infusion unit is in the shape of a conveniently shell that has an appearance of an arm cast. The integrated unit does not have external wiring or hoses between the infusion unit and the patient. The shell is also constructed to reduce rotation of the infusion unit on an arm where rotation can result in harm to the vein and can further damage internal medication and the operating mechanism. The unit is wrapped around the forearm and locked to the thumb holds it at a place. Unit is structured in such a way that the hardware is deep in the unit with cover to avoid accidental damage to the unit by water or electromagnetic or other element exposure to some extent. Material is such that it does not fracture with simple trauma to the infusion unit.

It is an object of the infusion unit to provide tightly regulated medication dosing that reduces the chance of overdosing. The dosing is provided with micro infusions such as Antibiotics and NS or Riger-lactate or TPN insulin and other replacement hormones. Because these are given under wireless controls to the infusion unit human error is virtually eliminated.

It is another object of the infusion unit to be used on out-patients where there is no need for a medication pole that can easily wrap around the body of the user the chance of accidentally pulling the needle from the arm is removed. There are no hoses that extend beyond the body of the infusion unit and any vein penetration is completely covered under the body of the infusion unit.

It is another object of the infusion unit to have a secure enclosed unit that has a secure enclosure to prevent unauthorized tampering and entry into the unit. Security of the internal medication is important when the infusion unit is not in a medical facility. The infusion unit can detect tampering and can notify authorities if the infusion unit is opened.

It is another object of the infusion unit to deliver the medication with a stepper motor for antibiotics of about 50 cc or larger or an infusion over a 24-hour period to an infusion of up to 500 cc or more.

It is still another object of the infusion unit to be used with medication dosing that can be remotely monitored, fusion resumed, changed by nursing and the patient. The infusion unit has a wireless connection to a network so in addition to the ability to adjust medication the vital signs of the patient, namely heart rate, O2 level and blood pressure can be monitored and recorded for review at the location of the patient or at a distal location. Unusual consumption of medication can be detected. Bluetooth communication can include a local alarm system as well as remote alarm system in case of any error. The communication can include security and protocol to prevent and provide notification of tampering. A global position sensor (GPS) can provide a user, doctor or hospital with a location, telemetry or other information.

Various objects, features, aspects, and advantages of the present invention will become more apparent from the following detailed description of preferred embodiments of the invention, along with the accompanying drawings in which like numerals represent like components.

BRIEF DESCRIPTION OF THE SEVERAL VIEWS OF THE DRAWING(S)

Figure 3:
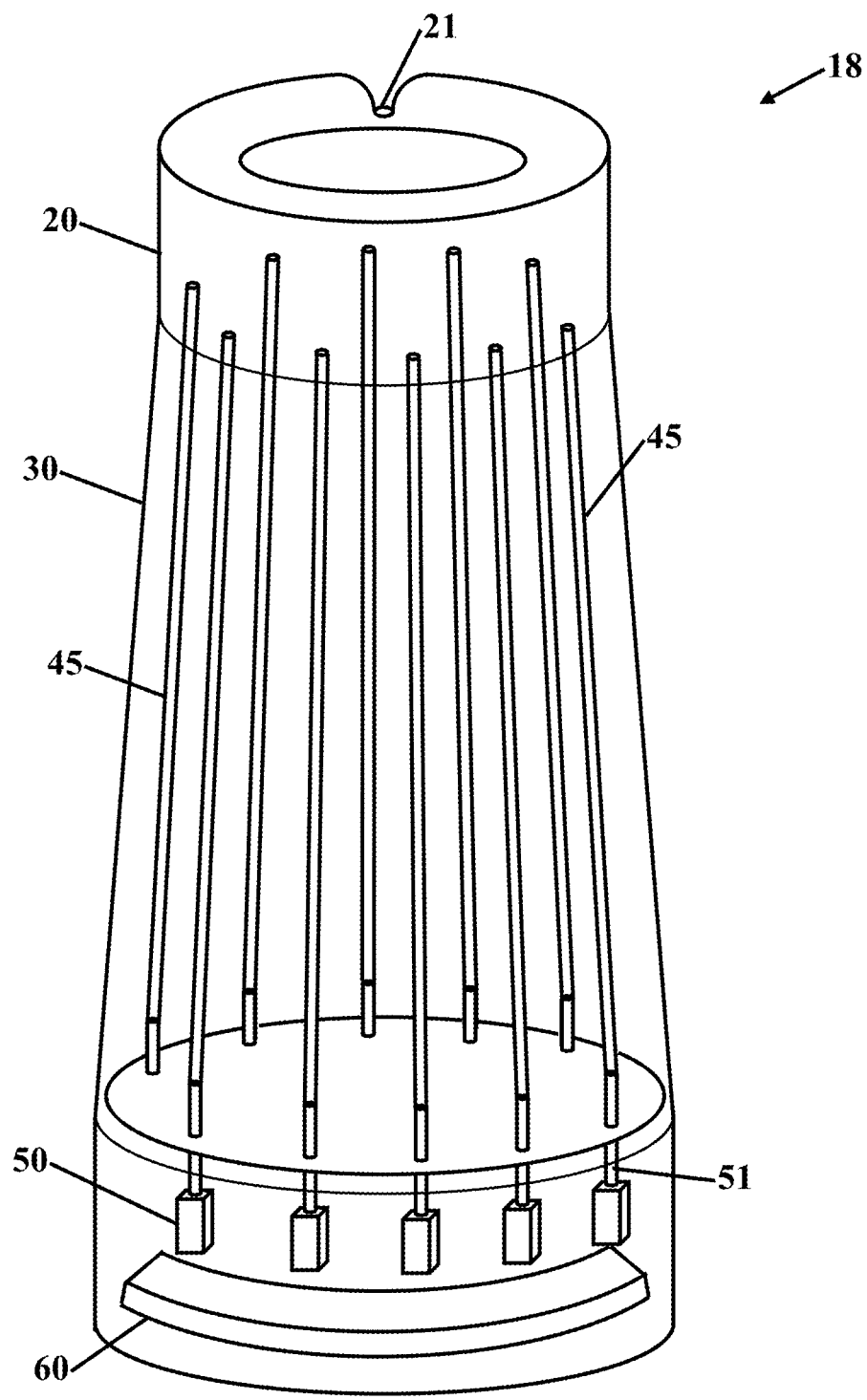
Figure 4:
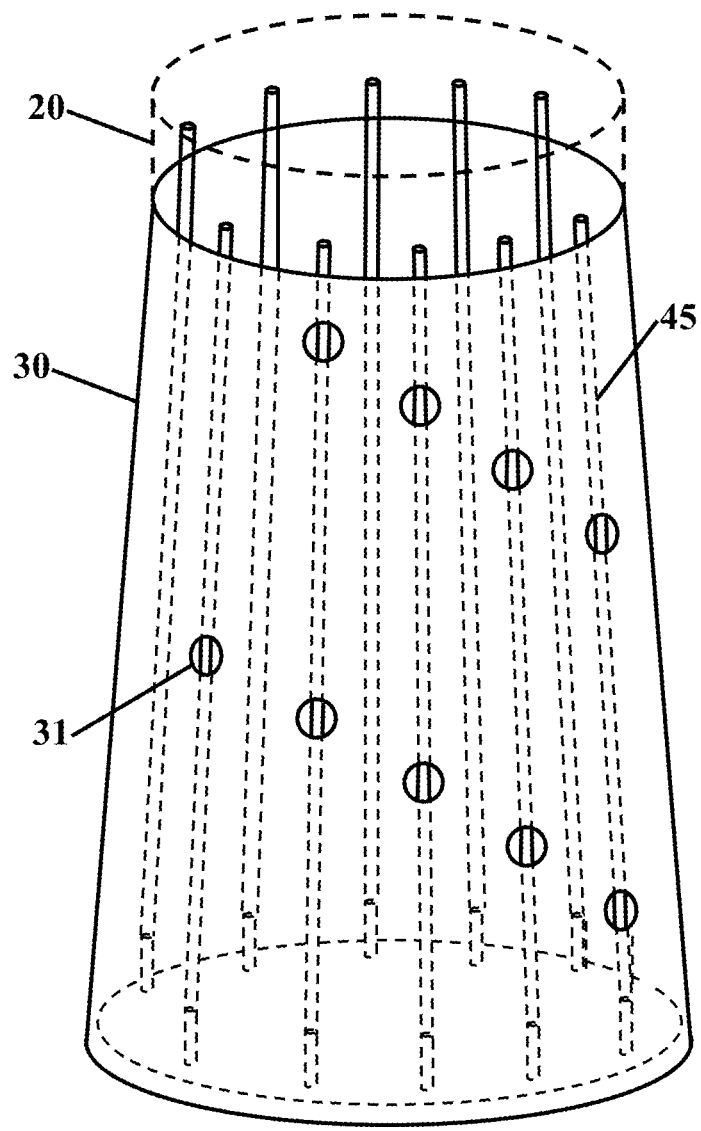
Figure 5:
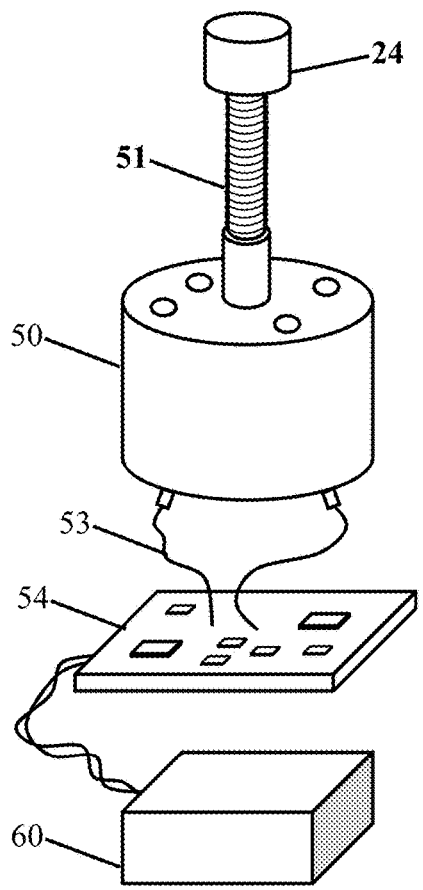
Figure 6:
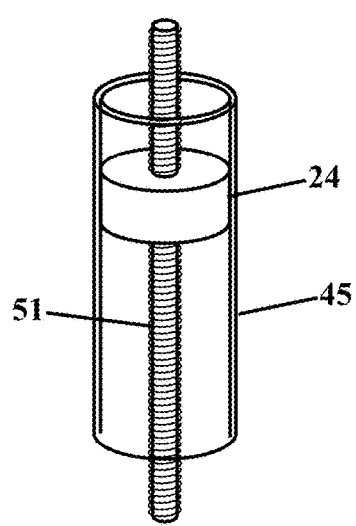
Figure 7:
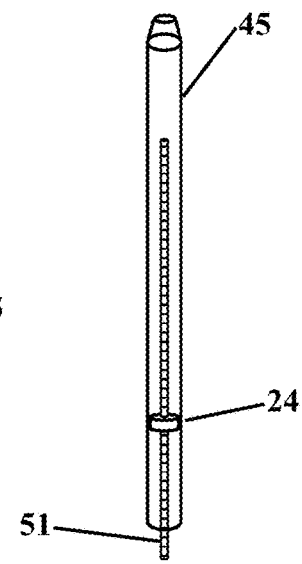
Figure 8:
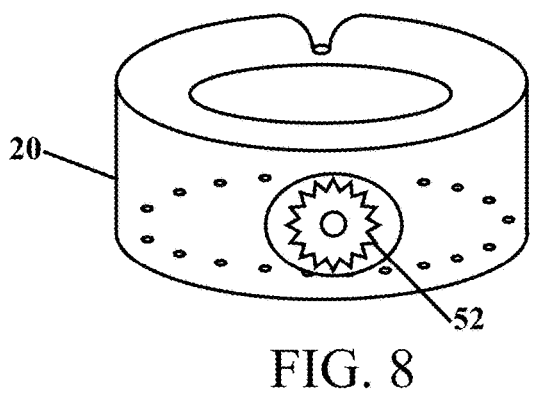
Figure 9:
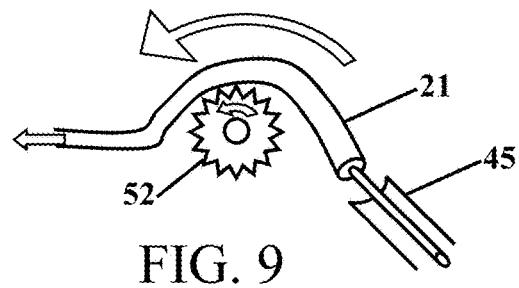
Figure 10:
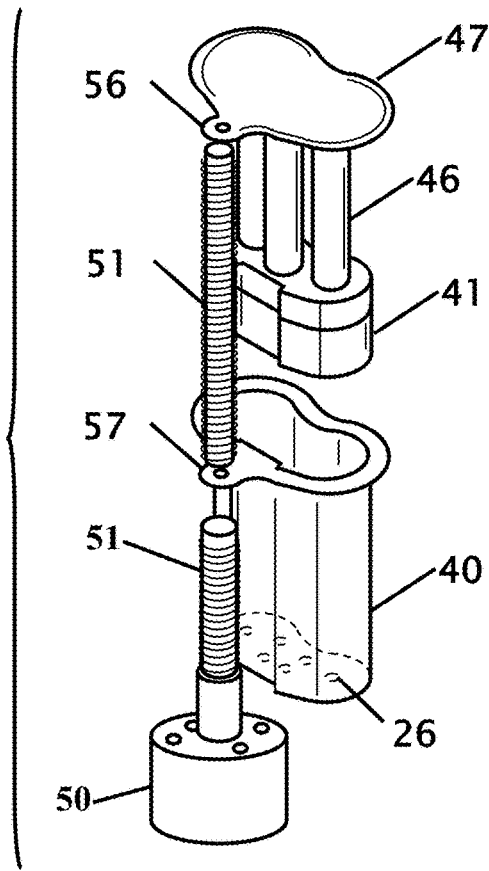
Figure 11:
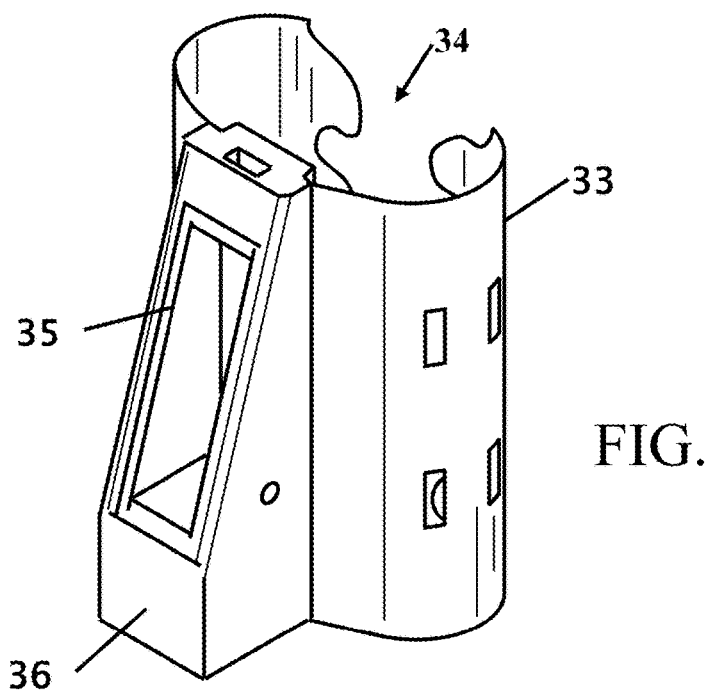
Figure 12:
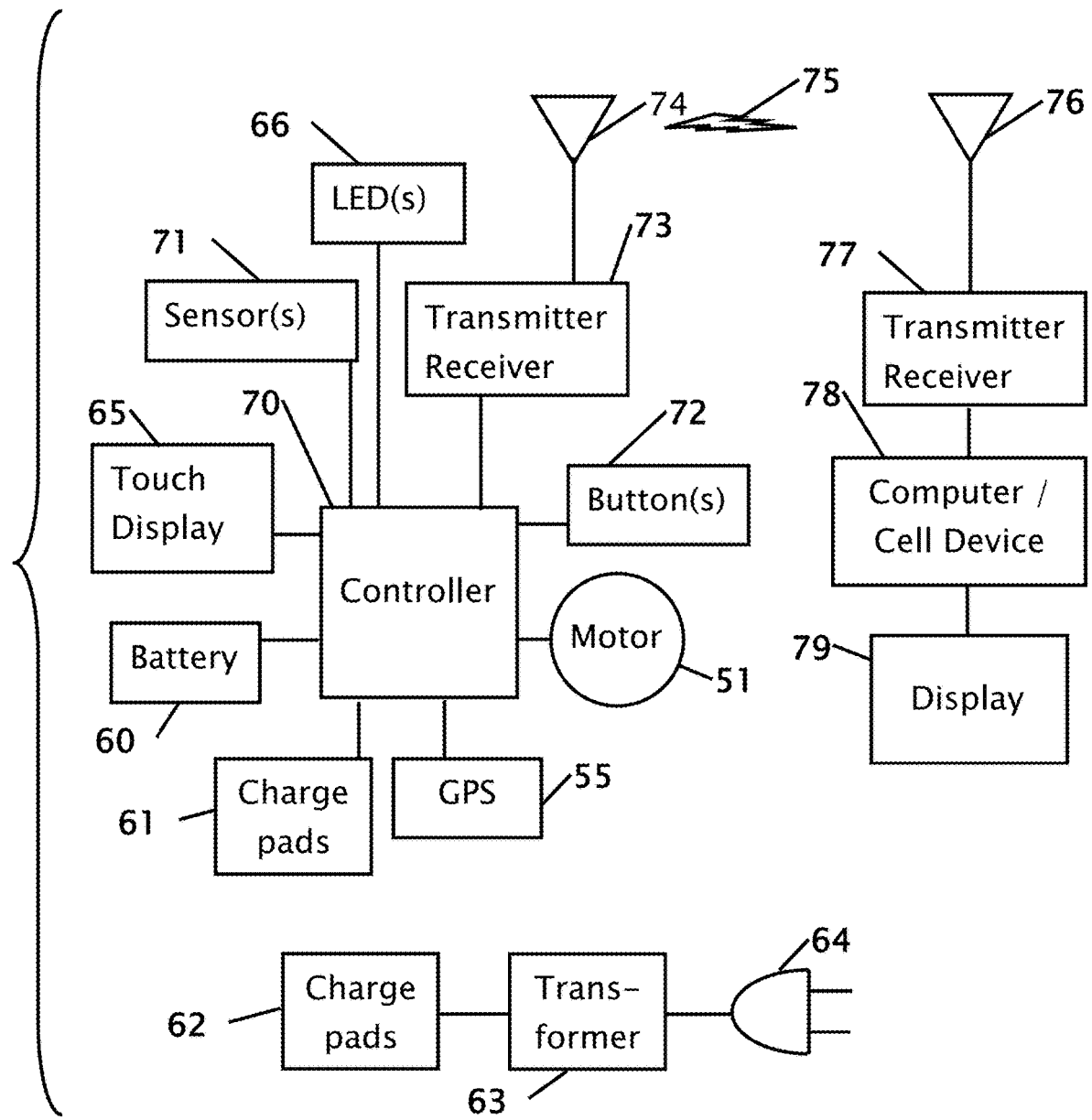
Figure 13:
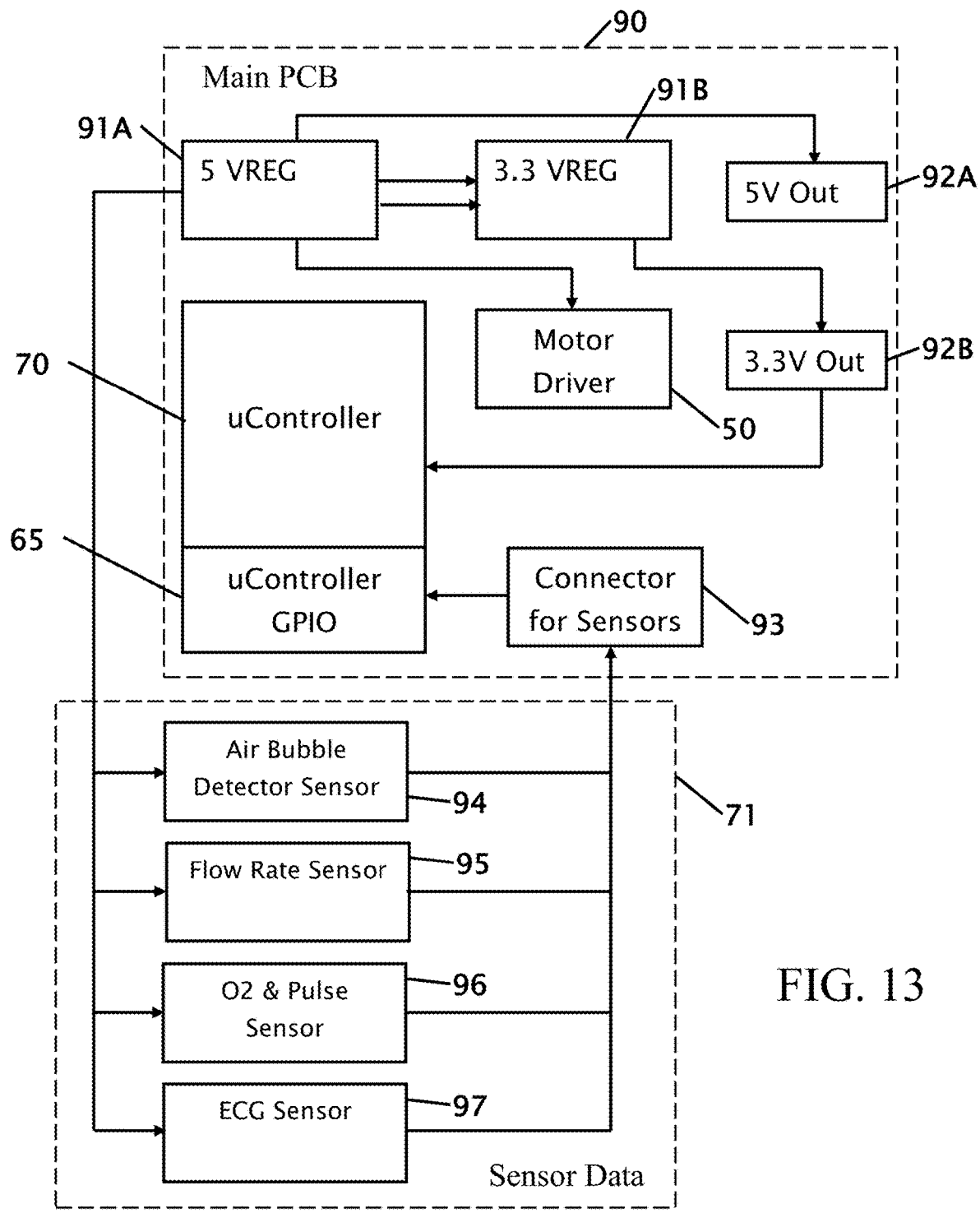
Figure 14:
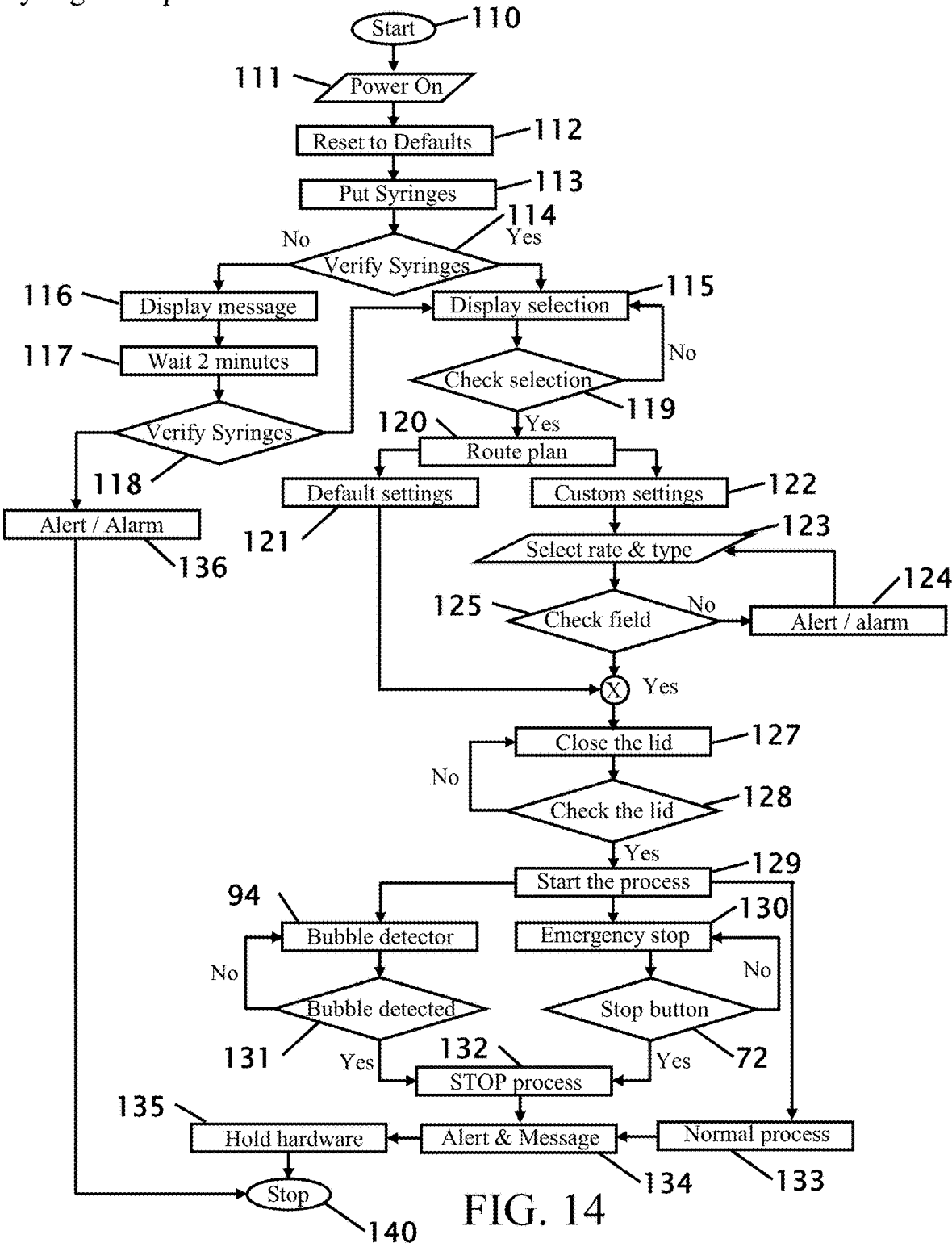
Figure 15:
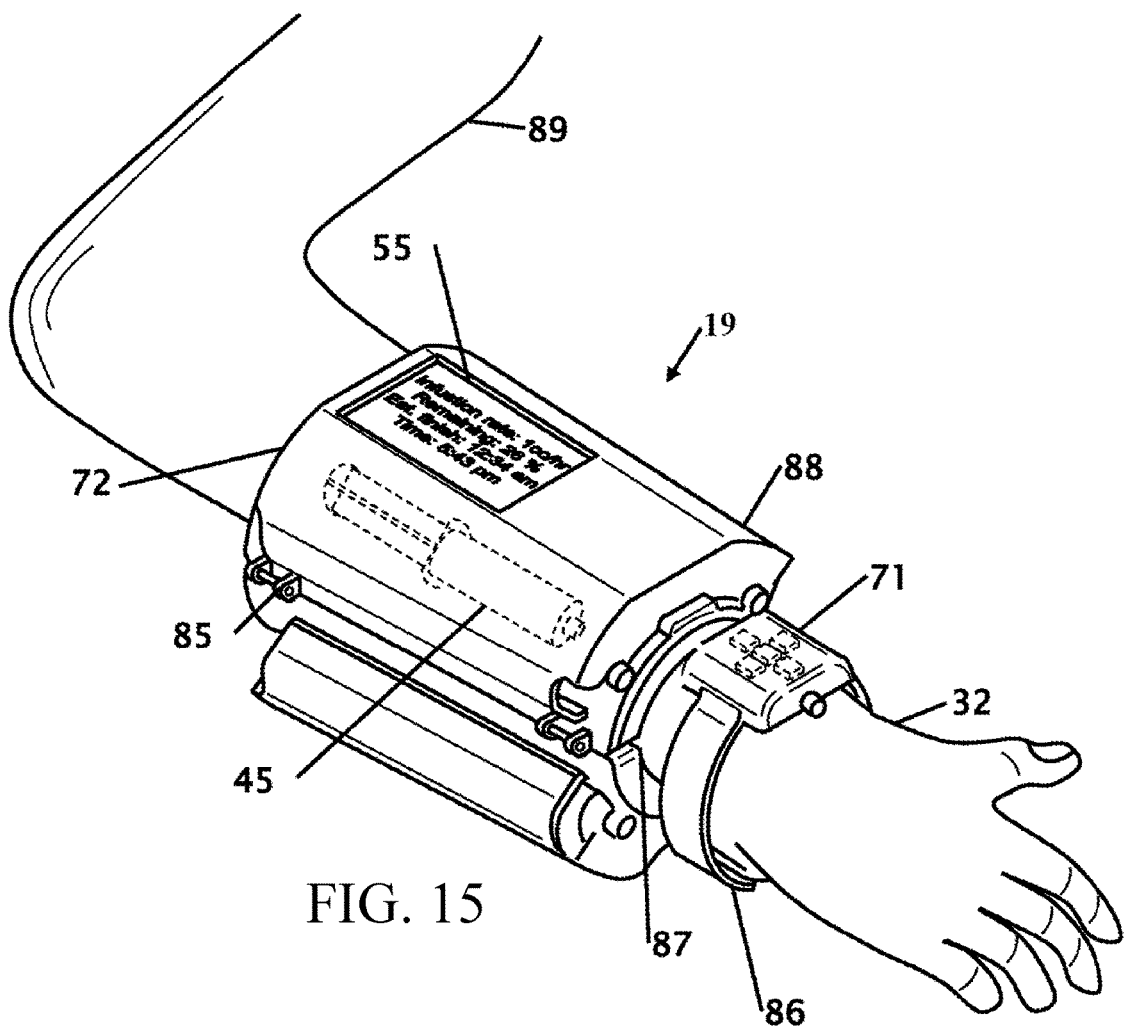
Figure 16:
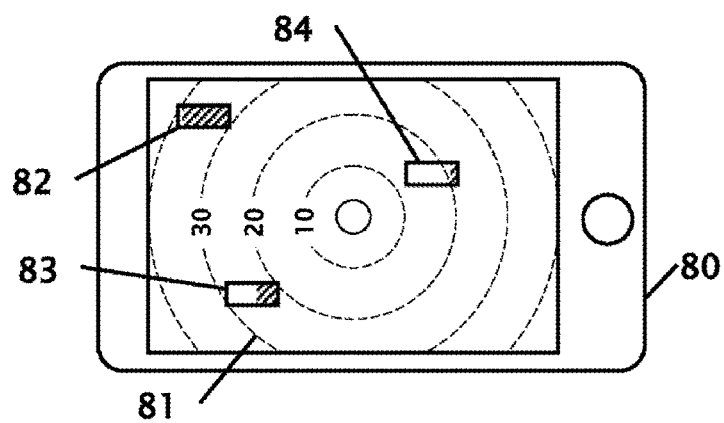

FIG. 1 shows a first embodiment of a large infusion unit.
FIG. 2 shows a reservoir with the drive system.
FIG. 3 shows a second embodiment of a micro infusion unit.
FIG. 4 shows a light case with disposable tubing.
FIG. 5 shows the drive system with a controller.
FIG. 6 shows the dispensing barrel.
FIG. 7 shows a Luer lock.
FIG. 8 shows a reservoir gear pump.
FIG. 9 shows the pump driving fluid into a vein.
FIG. 10 shows a large chamber plunger and chamber.
FIG. 11 the large chamber drive housing.
FIG. 12 shows a block diagram of the control electronics.
FIG. 13 shows an electrical block diagram.
FIG. 14 show a flow chart for the infusion unit.
FIG. 15 shows a patient wearing the infusion unit.
FIG. 16 shows a pictorial diagram of the doctor interface.

DETAILED DESCRIPTION OF THE INVENTION

It will be readily understood that the components of the present invention, as generally described and illustrated in the drawings herein, could be arranged and designed in a wide variety of different configurations. Thus, the following more detailed description of the embodiments of the system and method of the present invention, as represented in the drawings, is not intended to limit the scope of the invention, but is merely representative of various embodiments of the invention. The illustrated embodiments of the invention will be best understood by reference to the drawings, wherein like parts are designated by like numerals throughout.

| Item Numbers and Description | |
|---|---|
| 18 Micro infusion unit | 19 Large infusion unit |
| 20 reservoir | 21 IV line |
| 22 window | 23 bottom housing |
| 24 plunger | 25 inner layer |
| 26 exit holes | 30 outer shell |
| 31 holes | 32 outer shell |
| 33 middle shell | 34 plunger cavity |
| 35 drive cavity | 36 motor cavity |
| 40 large volume syringe | 41 curved seal |
| 42 plastic tubing | 43 disposable tubing |
| 44 seal | 45 vials |
| 46 plunger(s) | 47 plunger top |
| 50 stepper motor | 51 screw of stepper motor |
| 52 reservoir gear pump | 53 wiring |
| 54 circuit board | 55 display |
| 56 pull tab | 57 anchor tab |
| 60 battery | 62 charging pads |
| 63 transformer | 64 plug |
| 65 touch display | 66 LED(s) |
| 70 Arduino control system | 71 sensor(s) |
| 72 buttons | 73 transmitter/receiver |
| 74 antenna | 75 signal |
| 77 transmitter/receiver | 78 computer |
| 79 display | 80 computer |
| 81 distance | 82, 83, 84 infusion device |
| 85 hinge | 86 monitor strap |
| 87 lining | 88 security lock |
| 89 patient | 90 main PCB |
| 91 voltage regulator(s) | 92 voltage out |
| 93 connector | 94 air bubble detector |
| 95 flow rate sensor | 96 O2 & pulse sensor |
| 97 ECG sensor | 110 start |
| 111 power on | 112 reset to defaults |
| 113 put syringe | 114 verify syringe |
| 115 display selection | 116 display message |
| 117 wait | 118 verify syringe |
| 119 check selection | 120 route plan |
| 121 default settings | 122 custom settings |
| 123 select rate and type | 124 alert/alarm |
| 125 check field | 127 close lid |
| 128 check the lid | 129 start the process |
| 130 emergency stop | 131 bubble detected |
| 132 stop process | 133 normal process |
| 134 alert message | 135 hold hardware |
| 136 alert/alarm | 140 stop |

FIG. 1 shows a first embodiment of a large infusion unit 19 and FIG. 2 shows a reservoir with the drive system. The infusion unit has an appearance of an arm cast that is secured around an arm of a user with no exposed IV-lines that can be a source of infection and the IV-lines can't be accidental pull out of an arm. The inner layer 25 is an interior padded soft sponge styro-foam lining to give skin maximum comfort and keeps the infusion unit in place on an arm. The middle layer is the medication compartments with refillable chambers in a curve syringe compartment for a large chamber of medication or micro-syringes where one or more small volume chambers are located. The large chamber can have a volume of up to 125 cc or more. The smaller chamber can have up to 5 or more micro syringes with a volume of 5 cc or 10 cc. The outer shell 30 is the solid cover with protection of the syringes. In the preferred embodiment the infusion unit is constructed from light weight material of fiberglass material with plastic syringes. The infusion unit is constructed with side hinges (shown and described in other figures herein) so a forearm is placed and secure between the two halves of the unit.

Starting at the top of the large infusion unit 19 is a reservoir 20. The reservoir 20 preferably made from aluminum and has an IV-line access 21 that pushes fluid through the IV-line access 21 and in the vein of a patient. The IV-line access 21 is located under the reservoir 20 where it is protected from a user to gain access to the IV line and this also keeps the IV line in an area that prevents accidental harm. The central part of the body is an outer shell 30 that is a solid cover with protection for the syringe(s). The outer shell has hinges or locks to cover and secure the forearm therein. The entire unit is a strong light-weight construction. This provides structure for the housing and protection to the internal medication.

In this embodiment, the medication is contained within a large volume syringe 40 that has a volume of 100-500 cc. The large volume syringe 40 has a unique plastic curved syringe that has a curved seal 44. The bottom housing 23 includes the stepper motors 50, a controller and power supply, in this case Lithium Ion rechargeable batteries. Within the housing is a curved seal 44 that is driven by a screw axle 51 from a stepper motor 50. This figure shows three stepper motors 50, but as few as one or more can be used to drive the curved seal 44.

Another version of the large infusion unit 19 has one or two separate curved chambers located on opposite sides of the infusion unit. The two curved syringes are with 4 stepper motors 50 where two stepper motors are on each of the two curved syringes. The stepper motors 50 are with pancake unipolar leadscrew motors with 12 v Lithium battery powered and computer controlled reverse drive to reset the syringe to zero. The multiple stepper motors 50 ensures that the curved seal 44 is moved in a horizontal relationship. A microcontroller (not shown in this figure) connects the battery 60 to the stepper motor(s).

FIG. 3 shows a second embodiment of a micro infusion unit 18. The micro infusion unit 18 has a plurality of vials 45. As an example, there can be 10 vials 45, each having an internal volume of 25 cc for a total volume of 250 ml but other quantity of vials 45 and volumes are contemplated depending upon the mechanical design and the amount of medication that is required. The use of micro vials 45 allows for spacing the micro vials 45 around the circumference of the outer shell 30. The reservoir 20 in this embodiment collects the fluid from the vials 45 before the medication is passed into the IV line 21. While s single reservoir 20 is shown, there could be different reservoir that collect and pass fluids into the IV line 21. As an example, different medications can be dispensed in the day and a different blend dispensed in the evenings to assist a person in sleeping.

A plurality of stepper motors 50 are used in this embodiment. In this embodiment it is contemplated to use 10 stepper motors 50, with 5 motors placed on each side of the infusion unit. Each stepper motor 50 has a lead screw(s) 51. Once the medication has been depleted the lead screw(s) 51 can be reversed and returned to the initial position. While 5 injection units on each side is shown and disclosed, more or less than 5 drive systems per side is also contemplated.

Each syringe is 2 cc to 3 cc to give a total volume of between 20 and 3 cc, but syringes with larger or smaller volumes can also be used. The stepper motor pushes the syringe pistons one at a time or in any programmed sequence until the syringes emptying into the IV. There are sensors that detect when the syringes are empty or if air is present in the syringe and/or the delivery line.

A stepper motor 50 is located at the bottom of each vial 45. A screw of each stepper 51 drives medication from within the vial(s) 45 into the reservoir 20. A battery 60 connects the stepper motors 50 to the control electronics and can drive all of the stepper motors 50 in unison or sequentially. Detailed figures and descriptions of the different features are shown in the following figures.

FIG. 4 shows a light case with disposable tubing with a reservoir 20 shown in broken line at the dispensing end of the vials 45. The outer case is shown as an outer shell 30 that provides both structural strength and light weight. Because aluminum is not transparent a plurality of holes 31 are placed through the outer shell 30 so the level of fluid within the vials 45 can be viewed without opening the infusion unit. The holes 31 are shown in a spiral pattern but could also be placed linearly along the vials 45. There may also be indicia near the holes to allow for a visual measurement of the remaining medication in the vials 45.

FIG. 5 shows the drive system with a controller. The circuit board 54 that holds the controller is supplied power by the battery 60 and connects with wiring 53 to the stepper motor(s) 50. The batteries are replaceable or rechargeable using a phone charging device or an indictive charger. Stepper motors 50 provide a high level of accuracy and the output shaft of the stepper motors 50 is with a drive screw 51 that can incrementally drive the plunger 24.

The stepper motor(s) 50 provide accuracy in controlling and pushing the fluid in precise and calculated manner. Unique mechanism is built under the device floor which pushes piston 41 of the commercially available prefilled 60 cc syringe in a precise manner to move the fluid out of the syringe into the tubing and finally into the patient's blood stream. It is contemplated to use other low volume pump and large volume pump with separate designs.

Low Volume Pump (FRN) has a look of forearm cast with two prefilled syringes for a total of 4 stepper motors 50 (2 on each side). This embodiment is not shown. There is a pancake unipolar leadscrew motors with Lithium battery powered and computer controlled reverse drive to reset the syringe to zero.

FIG. 6 shows the dispensing barrel vial 45 and FIG. 7 shows a Luer lock. Arduino control system that will run in systemic way-system1 to system10 and once fluid is depleted the screw of the stepper motor 51 will run reverse by moving the plunger 24 back to its initial position. In this embodiment the vial 45 contains 25 cc of medication that is pushed with the plunger 24.

60 cc syringes (or other volume) is placed in the housing which fits on an adult forearm with a tube connected to an IV line. The housing supports and contains the stepper motor(s) 50 and a controlling module. The stepper motor 50 has long screw 51 attached to the piston of the syringe (shown in other figures herein. This pump is used with low volume precision infusions of antibiotics, hormonal replacements and other low volume drugs. The range of this device 2 cc/hr to 80 cc per hour. This rate of infusion is commonly used for patients who need antibiotics at home or in nursing home or hospitals.

FIG. 8 shows a reservoir gear pump and FIG. 9 shows the pump driving fluid into a vein. The vials connect into the bottom of the reservoir 20. In FIG. 8 the reservoir pump gear 52 is shown and in FIG. 9 the reservoir pump gear 52 is shown connecting between one of the vials 45 into the IV line 21 where the pump gear 52 can push the medication through the IV line 21 and into a patient.

FIG. 10 shows a large chamber plunger and chamber and FIG. 11 the large chamber drive housing. This is a high-volume pump (FRN) that uses a unique kidney shaped syringe (MRZ) with a capacity of 400 cc that could be wrapped around the forearm via forearm stabilizer. The plunger top 47 of the slider will wrap around the syringe. The plunger top 47 slider has on top of its stepper motor 50 and controlling hardware. The motor 50 drives a screw 51 mechanism that pulls the curved seal 41 of the syringe piston thus pushing the fluid out of the syringe into the tubing which will go into the IV line and into the patient's veins. The bottom of the large volume syringe 40 has a plurality of exit holes 26 to decrease the thrust pressure and increase the desired output. The multiple exit holes can be combined into a single IV line. This embodiment can be used in the field by EMS for injured patients or in the battlefield for soldiers.

The middle shell 33 in FIG. 11 houses the drive system, plunger and syringe. The plunger and syringe fit within the plunger cavity 34. The drive motor fits within the motor cavity 36 and the drive screw connects to the tabs on the plunger and syringe within the drive cavity 35.

The high-volume infusion unit is shown with prefilled 400 cc syringe(s) wrapped only on the dorsal aspect of the forearm and stabilizing plastic board on the other side of the forearm tied by hook and loop bands on either side. The infusion unit can be used in the field such as battlefield injured soldiers without need for a pole and IV bag.

FIG. 12 shows a block diagram of the control electronics. The controller 70 includes an Arduino control system to dispense medication. The controller can have buttons 72 and an optional display as a user interface at the infusion unit. The user interface can include a touch display 65 or a non-touch display. One or a plurality of status LED's 66 for status. One or more sensors 71 can monitor fluid levels in the medication and can include patient vital signs, including, but not limited to heart rate, O2 and blood pressure. The sensor(s) that are present can detect when a syringe has air or is empty. The infusion unit can include GPS 55 to track the patient and the infusion unit for security and to easily locate a patient. The infusion unit is powered by batteries 60 that can be recharged with charging pads 61 or with inductive charging. While the infusion unit is self-contained a transmitter/receiver unit 73 with an antenna 74 allows for changing or monitoring the patient and the infusion unit through wired or wireless communication.

The communication can be with Bluetooth, WIFI or cellular connection to a programming and/or monitoring device. The programming and/or monitoring device has an antenna 76 connected to a transmitter/receiver 77 module. A computer 78, cellular device, wireless device, tablet or phone device has a display 79 and user interface to program and/or monitor the infusion device. One example is shown and described in the following figures.

FIG. 13 shows an electrical block diagram. This block diagram has a main PCB 90 block and a sensor data block 71. Unregulated voltage is regulated with a 5-volt regulator 91A that drives the motor 50 and a 3.3-volt regulator 91B that powers the sensors and the controller 70. There may also be voltage outputs for 5 volts 92A and 3.3 volts 92B. In one contemplated embodiment an Arduino control system is used. The controller 70 is shown connected to a touch display 65 to show information to a doctor, user or care giver and to also allow for the user to select/enter information. A connector 93 provides an electrical connection to the sensors.

The sensor data block 71 has connections for at least one of an air bubble detector sensor 94 that can detect if air is in the IV line. A flow rate sensor 95 ensures that medication is being supplied at the proscribed rate. The infusion device can also monitor vital signs of a user and can include at least one of O2 sensor, pulse sensor 96, blood pressure and electrocardiogram sensor ECG 97.

FIG. 14 show a flow chart for the infusion unit. The infusion units starts 110 when power is turned on 111. As the infusion unit starts it will perform reset to defaults 112 setting. The infusion unit will check is if at least one syringe 113 is installed and will verify the presence of at least one syringe 114. If there is no syringe then a message will be displayed 116 on the screen. The infusion unit will wait a period of time, in this example 2 minutes 117 and will again check if a syringe has been installed the verify the presence of at least one syringe. 118. If a syringe has not been installed an alert or alarm 136 can be shown or an audible alarm can be announced. While a 2-minute delay is shown, this can be any appropriate period of time.

If a syringe is detected, the infusion unit can have a scanner that can read the type of medication from a barcode or other visual or RFID indicator on the medication syringe. The infusion unit can match the barcode or RFID to a suggested medication or to a patient record to load settings. When a syringe is installed the infusion unit will then show the display selection 115 and will check the proscribed selection 119. The selection will then set a route plan 120. The doctor or other provider can make a custom setting 112 or allow for the default setting 121. IN the custom setting 122 the rate and type 123 of the medication is entered.

One or more rates of injection are checked, set or selected 125 and if all of the data is not properly entered an alert and/or alarm 124 can be made. The infusion unit will verify that the lid of the infusion unit has been closed 127 or the user can be prompted to close the lid. The infusion unit will check and verify that the lid has been closed 128 to allow the infusion unit to start the process 129 of injecting the medication.

While the medication is being injected the infusion unit will monitor the flow of medication to check the IV line for air bubbles 94 and is an air bubble is detected 131 the process is stopped 132. The process can also be stopped if a person presses and emergency stop 130 by pressing a stop button 72. Both of these events will stop the process 132. There are other contemplated scenarios where the process can be stopped, including but not limited to the normal process 133 completing, if the medication stops flowing, or if the vital signs of the person exceed a proscribed safe level.

When the process of the infusion unit stops there is an alert and message 134. The hardware is placed on a hold 135 position to prevent further injection of medication and the process will come to a stop 140.

FIG. 15 shows a patient wearing the infusion unit and FIG. 16 shows a pictorial diagram of the doctor interface. From obvious look the infusion device 19 has similarity to having a cast on an arm of a patient 89, secure no tubing and no exposed IV-line therefore there is less chance of infection or accidental pull. Outer shell 32 is the solid cover with protection of the syringes. A middle layer with medication compartments with refills and curve syringe compartment or micro-syringe. The interior is a soft sponge styro-foam lining 87 to give skin maximum comfort and yet keep the infusion unit 19 in place. The infusion unit 19 will remain light weight due to use of fiberglass material and plastic syringes. The infusion unit will have a side hinges 85 thus the forearm is in between the two halves of the unit. A security lock 88 holds the halves together and prevents tampering. The housing with the sensors 71 that includes the pulse sensor, flow meter, air bubble detector and the EKG sensor is shown.

Within the infusion device is a soft sponge styro-foam lining 87 to give skin maximum comfort and yet keep the infusion unit 19 in place. The infusion unit is shown with a monitor strap 86 where heart rate O2 and other patient vital signs can be monitored with minimal noise and motion interference from the drive motor. It is also contemplated that there can be a thumb hole that further locks the infusion unit onto the forearm of the patient and prevent rotation of the infusion unit to reduce the chance that the IV is disturbed. The infusion device can have a security lock 88 to prevent tampering or removal. This figure shows an optional display 55 or touch display and buttons 72 (not visible) that can be used for programming or locally viewing information regarding the medication within the infusion unit 19.

This figure shows a common syringe vial 45 being used in the infusion device. The syringe vial 45 can be filled with medication and inserted into the infusion device where the drive system can inject the medication from within the syringe vial 45. After use the syringe vial 45 can be disposed using normal medical disposal practices.

A doctor or other medical person can view status or make changes using a computer, tablet, or in FIG. 16 a cellular phone 80. This figure shows rings for the distance 81 between the cellular device 80 and a plurality of infusion units 82, 83 and 84. Each of the infusion units shows a graphical image of the remaining medication. A doctor can select an individual infusion unit to view additional information and make changes from a distance. Changes can be logged, time stamped and stored for future reference.

Thus, specific embodiments of an infusion unit have been disclosed. It should be apparent, however, to those skilled in the art that many more modifications besides those described are possible without departing from the inventive concepts herein. The inventive subject matter, therefore, is not to be restricted except in the spirit of the appended claims.

The invention claimed is:

1. An infusion unit comprising:
   a cylindrical housing that is configured to be secured around an arm of a person;
   said infusion unit further including at least one internal reservoir for temporally holding a medication;
   a connection from said at least one internal reservoir to an IV needle;
   a dispensing mechanism that forces said medication from within said at least one internal reservoir through said IV needle;
   said at least one internal reservoir is kidney shaped and has a plurality of exit holes that connect to said IV needle, and
   a controller that operates said dispensing mechanism.

2. The infusion unit according to claim 1, further includes at least one monitoring sensor that is configured to monitor at least one vital sign of said person.

3. The infusion unit according to claim 2, wherein said vital sign is selected from a group consisting of a heart rate, an O2 content, blood pressure and electrocardiogram.

4. The infusion unit according to claim 1, wherein said dispensing mechanism is a motor.

5. The infusion unit according to claim 4, wherein said motor is a stepper motor that moves a syringe piston.

6. The infusion unit according to claim 1, further includes an interface that allows said controller to be programmed externally from said cylindrical housing.

7. The infusion unit according to claim 1, further includes a touch display.

8. The infusion unit according to claim 1, wherein said at least one internal reservoir has an internal volume of 250 ml or greater.

9. The infusion unit according to claim 1, wherein there are at least two reservoirs.

10. The infusion unit according to claim 9, wherein each of said at least two reservoirs have an internal volume of 5 cc or less.

11. The infusion unit according to claim 1, wherein said cylindrical housing has an interior padded liner.

12. The infusion unit according to claim 1, further includes a flow sensor.

13. The infusion unit according to claim 1, further includes an air bubble sensor.

14. The infusion unit according to claim 1, further includes an outer shell with a hinge and a lock.

15. The infusion unit according to claim 1, further includes a sensor that detect a presence of said at least one internal reservoir.

16. The infusion unit according to claim 1, further includes an internal power supply.

17. The infusion unit according to claim 1, further includes a wireless connection to an external communication device.

18. The infusion unit according to claim 1, further includes a scanner that is configured to read a content of said at least one internal reservoir.

19. The infusion unit according to claim 1, further includes a tamper detection mechanism.

20. The infusion unit according to claim 1, further includes a global positioning system (GPS).

* * * * *